(12) United States Patent
Kim et al.

(10) Patent No.: US 9,897,552 B2
(45) Date of Patent: Feb. 20, 2018

(54) OPTICAL TRANSFORMATION MODULE AND OPTICAL MEASUREMENT SYSTEM, AND METHOD OF MANUFACTURING A SEMICONDUCTOR DEVICE USING OPTICAL TRANSFORMATION MODULE AND OPTICAL MEASUREMENT SYSTEM

(71) Applicant: Samsung Electronics Co., Ltd., Suwon-si (KR)

(72) Inventors: Tae-Joong Kim, Hwaseong-si (KR); Yong-Deok Jeong, Hwaseong-si (KR); Kwang-Soo Kim, Pyeongtaek-si (KR); Byeong-Hwan Jeon, Yongin-si (KR); Yu-Sin Yang, Seoul (KR); Sang-Kil Lee, Yongin-si (KR); Chung-Sam Jun, Suwon-si (KR)

(73) Assignee: SAMSUNG ELECTRONICS CO., LTD., Yeongtong-gu, Suwon-si, Gyeonggi-do (KR)

(*) Notice: Subject to any disclaimer, the term of this patent is extended or adjusted under 35 U.S.C. 154(b) by 215 days.

(21) Appl. No.: 14/805,439

(22) Filed: Jul. 21, 2015

(65) Prior Publication Data

US 2016/0018328 A1    Jan. 21, 2016

(30) Foreign Application Priority Data

Jul. 21, 2014   (KR) .................. 10-2014-0091807

(51) Int. Cl.
*G01N 21/47*   (2006.01)
*G01N 21/95*   (2006.01)
(Continued)

(52) U.S. Cl.
CPC ..... *G01N 21/9501* (2013.01); *G02B 26/0808* (2013.01); *G02B 3/0006* (2013.01); *G02B 21/0016* (2013.01)

(58) Field of Classification Search
CPC ........... G01N 21/4738; G01N 21/9501; G01N 2201/068; G01N 2201/06113; G02B 26/0808; G02B 3/0006
See application file for complete search history.

(56) References Cited

U.S. PATENT DOCUMENTS 4,979,123 A * 12/1990 Yang .................... G01J 3/06
356/301
5,471,066 A   11/1995 Hagiwara
(Continued)

FOREIGN PATENT DOCUMENTS

JP    3775861 B2   5/2006
JP    3861666 B2   12/2006
(Continued)

*Primary Examiner* — Sang Nguyen
(74) *Attorney, Agent, or Firm* — Muir Patent Law, PLLC

(57) ABSTRACT

An optical transformation module includes a light generator generating a parallel light beam to be incident onto a surface of an inspection object and changing a wavelength of the parallel light beam, and a rotating grating positioned on a path of the parallel light beam and rotatable by a predetermined rotation angle such that the parallel light beam is transformed according to the wavelength of the parallel light beam and the rotation angle of the rotating grating to have a desired incidence angle and a desired incidence position onto the surface of the inspection object.

8 Claims, 8 Drawing Sheets

(51) Int. Cl.
  *G02B 26/08*  (2006.01)
  *G02B 3/00*  (2006.01)
  *G02B 21/00*  (2006.01)

(56) References Cited

U.S. PATENT DOCUMENTS

| | | | | |
|---|---|---|---|---|
| 5,986,780 | A * | 11/1999 | Sudo | G03H 1/08 |
| | | | | 359/22 |
| 6,272,269 | B1 * | 8/2001 | Naum | G02B 6/0026 |
| | | | | 362/551 |
| 7,372,565 | B1 | 5/2008 | Holden et al. | |
| 8,319,971 | B2 | 11/2012 | Shyu et al. | |
| 2009/0040906 | A1 * | 2/2009 | Hong | G11B 7/0908 |
| | | | | 369/112.23 |
| 2010/0033730 | A1 * | 2/2010 | Kim | G01B 9/02004 |
| | | | | 356/479 |
| 2010/0254237 | A1 * | 10/2010 | Fujita | B82Y 10/00 |
| | | | | 369/47.49 |
| 2010/0315597 | A1 * | 12/2010 | Powell | G02B 26/08 |
| | | | | 353/20 |
| 2010/0321704 | A1 * | 12/2010 | Kawai | G01B 11/24 |
| | | | | 356/612 |
| 2013/0128268 | A1 | 5/2013 | Tomioka | |
| 2013/0272501 | A1 * | 10/2013 | Yamaguchi | A61B 6/00 |
| | | | | 378/84 |

FOREIGN PATENT DOCUMENTS

| | | |
|---|---|---|
| JP | 2007-199397 A | 8/2007 |
| JP | 2013-068551 A | 4/2013 |
| KR | 10-2013-0134279 A | 12/2013 |
| KR | 10-1356707 B1 | 2/2014 |

\* cited by examiner

OPTICAL TRANSFORMATION MODULE AND OPTICAL MEASUREMENT SYSTEM, AND METHOD OF MANUFACTURING A SEMICONDUCTOR DEVICE USING OPTICAL TRANSFORMATION MODULE AND OPTICAL MEASUREMENT SYSTEM

PRIORITY STATEMENT

This application claims priority under 35 U.S.C. § 119 to Korean Patent Application No. 10-2014-0091807, filed on Jul. 21, 2014 in the Korean Intellectual Property Office (KIPO), the contents of which are herein incorporated by reference in their entirety.

BACKGROUND

1. Field

The present disclosure relates to an optical transformation module and an optical measurement system. More particularly, the present disclosure relates to an optical transformation module for inspecting defects of semiconductor devices and an optical measurement system including the same. The disclosure also relates to a method of manufacturing a semiconductor device using an optical transformation module and optical measurement system.

2. Description of the Related Art

Generally, minute defects of semiconductor wafers may be detected using bright-field optical microscopes. In an optical microscope, a light may be incident onto a surface of the wafer and a reflecting light from the surface may be collected to detect a defect on the wafer surface. When a light is incident onto the surface at a specific incidence angle, the defects may be detected more clearly due to kinds of the defects and a shape of a minute pattern.

In a conventional angle scatterometer, a light may be incident onto a surface of the wafer at various incidence angles using a space filter. However, optical losses of the light passing through the space filter may be increased greatly, thereby deteriorating detection efficiency. Additionally, because a change speed of the incidence angle by the space filter is very slow, inspecting with various incidence angles on the whole surface of the wafer may require a significant amount of time, thereby lowering overall productivity.

SUMMARY

Example embodiments provide an optical transformation module capable of providing high defect detection efficiency and reducing light losses.

Example embodiments provide an optical measurement system including the optical transformation module.

Example embodiments also describe a method of manufacturing a semiconductor device using an optical transformation module and optical measurement system.

According to example embodiments, an optical transformation module include a light generator generating a parallel light beam to be incident onto a surface of an inspection object and changing a wavelength of the parallel light beam, and a rotating grating positioned on a path of the parallel light beam and rotatable by a predetermined rotation angle such that the parallel light beam is transformed according to the wavelength of the parallel light beam and the rotation angle of the rotating grating to have a desired incidence angle and a desired incidence position onto the surface of the inspection object.

In one embodiment, the rotating grating may include a plurality of regions which are arranged alternately in a direction and have different refractive indices respectively.

In one embodiment, the rotating grating may include a plurality of regions which are arranged alternately in a direction and have different transmittances respectively.

In one embodiment, the rotating grating may have a striped or grid pattern.

In one embodiment, the light generator may include a light source generating a light and changing a wavelength of the light and a collimating lens positioned on a path of the light to convert the light into the parallel light beam having the wavelength.

In one embodiment, the light generator may include a laser source which generates a laser beam and changes a wavelength of the laser beam According to example embodiments, an optical measurement system include an optical transformation module generating a parallel light beam to be incident onto a surface of an inspection object and adjusting an incidence angle and the incidence position of the parallel light beam with respect to the surface and a collector collecting a reflecting light beam from the surface of the inspection object. The optical transformation module include a light generator generating the parallel light beam and changing a wavelength of the parallel light beam and a rotating grating positioned on a path of the parallel light beam and rotatable such that the parallel light beam is transformed according to the wavelength of the parallel light beam and the rotation angle of the rotating grating to have a desired incidence angle and a desired incidence position onto the surface of the inspection object.

In one embodiment, the rotating grating may include a plurality of regions which are arranged alternately in a direction and have different refractive indices respectively.

In one embodiment, the rotating grating may include a plurality of regions which are arranged alternately in a direction and have different transmittances respectively.

In one embodiment, the rotating grating may have a striped or grid pattern.

In one embodiment, the light generator may include a light source generating a light and changing a wavelength of the light and a collimating lens positioned on a path of the light to convert the light into the parallel light beam having the wavelength.

In one embodiment, the light generator may include a laser source which generates a laser beam and changes a wavelength of the laser beam.

In one embodiment, the optical measurement system may further include a lens array through which the parallel light beam is incident onto the surface of the inspection object at the incidence and the incidence position, the lens array may include a focusing lens positioned on a path of the parallel light beam passing through the rotating grating to convert the parallel light beam into a convergent/divergent light beam, an objective lens positioned on a path of the convergent/divergent light beam to convert again the convergent/divergent light beam into the parallel light beam, direct the parallel light beam to the inspection object at the incidence angle and the incidence position, and convert a light beam reflecting from the inspection object into a reflecting parallel light beam, and an ocular lens positioned on a path of the reflecting parallel light beam to convert the reflecting parallel light beam into a reflecting light beam.

In one embodiment, the optical measurement system may further include a beam splitter which is positioned between the focusing lens and the objective lens to reflect the convergent/divergent light beam passing through the focusing lens to the objective lens.

In one embodiment, the reflecting light beam may have image information of the inspection object, and the collector comprises a charge coupled device (CCD) lens for collecting the image information of the inspection object from the reflecting light beam.

According to example embodiments, a method of manufacturing a semiconductor device using an optical transformation module includes: providing a semiconductor chip; emitting, from a light generator, a parallel light beam for scanning the semiconductor chip, the parallel light beam having a wavelength selected using the light generator; receiving the parallel light beam as an incident parallel light beam at a light-beam aiming device, and aiming the parallel light beam by the light-beam aiming device so that the parallel light beam exiting the light-beam aiming device has a vector direction different from the direction of the incident parallel light beam. The vector direction of the parallel light beam is changed according to the selected wavelength of the parallel light beam and the positioning of the light-beam aiming device. The method further includes passing the parallel light beam through a lens array; using the light output from the lens array to scan the semiconductor chip; and based on the scanning, determining whether the semiconductor chip passes or fails inspection.

In one embodiment, the light-beam aiming device is a grating, and the vector direction of the parallel light beam is changed according to the selected wavelength of the parallel light beam and a positioning of the grating.

In one embodiment, the light-beam aiming device is a rotating grating, and the vector direction of the parallel light beam is changed according to the selected wavelength of the parallel light beam and an amount of rotation of the rotating grating.

In one embodiment, the rotating grating comprises a plurality of regions, which are arranged alternately in a direction and have different refractive indices and/or different transmittances respectively.

In one embodiment, the rotating grating has a striped or grid pattern.

In one embodiment, the light-beam aiming device is used to control a light beam incident on the semiconductor chip to have a desired incidence angle and a desired incidence position on the surface of the semiconductor chip.

In one embodiment, the light beam incident on the semiconductor chip is reflected by the semiconductor device; the reflected light passes through the lens array; and the light exiting the lens array has image information of the semiconductor chip and is collected on a collector for inspection.

In one embodiment, when the semiconductor chip passes inspection, the semiconductor chip is mounted on a substrate.

In one embodiment, the substrate is a package substrate, and when the semiconductor chip passes inspection, the semiconductor chip is covered with a protective mold.

In one embodiment, when the semiconductor chip passes inspection, the semiconductor chip is included in a package or module.

According to certain aspects of the disclosed embodiments, a method of manufacturing a semiconductor device includes: providing a semiconductor chip; emitting, from a light generator, a parallel light beam for scanning the semiconductor chip, the parallel light beam having a wavelength selected using the light generator; receiving the parallel light beam as an incident parallel light beam at a light-beam aiming device, and aiming the parallel light beam by the light-beam aiming device to change an incidence angle and position of the parallel light beam exiting the light-beam aiming device. The combination of the incidence angle and position of the parallel light beam is changed according to the selected wavelength of the parallel light beam and the positioning of the light-beam aiming device. The method additionally includes passing the parallel light beam through a lens array; using the light output from the lens array to scan the semiconductor chip; and based on the scanning, determining whether the semiconductor chip passes or fails inspection.

In one embodiment, the light-beam aiming device is a grating, and the position of the parallel light beam is changed according to the positioning of the grating.

In one embodiment, the light-beam aiming device is a rotating grating, and the position of the parallel light beam is changed according to an amount of rotation of the rotating grating.

In one embodiment, the angle of the parallel light beam is changed according to the selected wavelength of the parallel light.

In one embodiment, the light output by the lens array is reflected by the semiconductor device; the reflected light passes through the lens array; and the light exiting the lens array has image information of the semiconductor chip and is collected on a collector for inspection.

In one embodiment, when the semiconductor chip passes inspection, the semiconductor chip is mounted on a substrate.

In one embodiment, the substrate is a package substrate, and the method additionally includes: when the semiconductor chip passes inspection, covering the semiconductor chip with a protective mold.

According to other aspects of the disclosed embodiments, a method of manufacturing a semiconductor device includes providing a semiconductor chip; emitting, from a light generator, a parallel light beam for scanning the semiconductor chip, the parallel light beam having a wavelength selected using the light generator; receiving the parallel light beam as an incident parallel light beam at a rotating grating, and using the rotating grating, along with the selected wavelength, to change an incidence angle and position of the parallel light beam exiting the rotating grating; passing the parallel light beam through a lens array; using the light output from the lens array to scan the semiconductor chip; and based on the scanning, determining whether the semiconductor chip passes or fails inspection.

In one embodiment, when the semiconductor chip passes inspection, the semiconductor chip is mounted on a substrate.

In one embodiment, the substrate is a package substrate, and the method further includes: when the semiconductor chip passes inspection, covering the semiconductor chip with a protective mold.

BRIEF DESCRIPTION OF THE DRAWINGS

Example embodiments will be more clearly understood from the following detailed description taken in conjunction with the accompanying drawings.

FIG. 1 is a schematic diagram illustrating an optical measurement system in accordance with example embodiments.

FIG. 2 is an enlarged perspective view illustrating an 'A' portion in FIG. 1 in accordance with an example embodiment.

FIG. 3 is a perspective view illustrating a rotating grating of the optical measurement system in FIG. 1 in accordance with an example embodiment.

FIG. 4 is a view illustrating a parallel light beam incident onto an inspection object in FIG. 1 in accordance with an example embodiment.

FIG. 5 is an enlarged view illustrating a 'B' portion in FIG. 1 in accordance with an example embodiment.

FIG. 6 is an enlarged view illustrating a 'C' portion in FIG. 1 in accordance with an example embodiment.

FIG. 7 is a flowchart illustrating an optical measurement method in accordance with example embodiments.

FIG. 8 is a flowchart illustrating a method of a manufacturing a semiconductor device in accordance with example embodiments.

DETAILED DESCRIPTION OF EXAMPLE EMBODIMENTS

Figure 1:
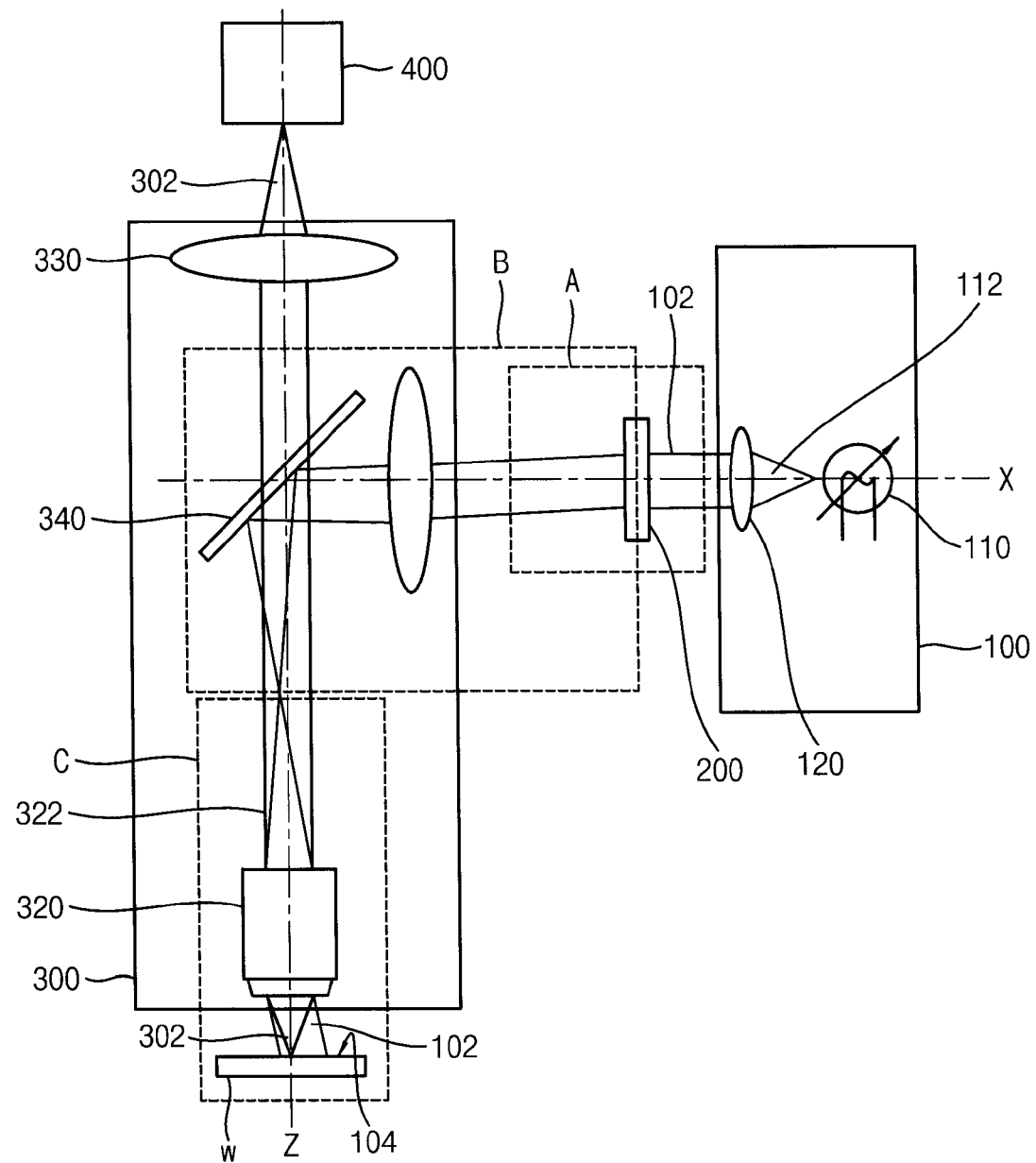
FIGS. 1 to 8 represent non-limiting, example embodiments as described herein.

Various example embodiments will be described more fully hereinafter with reference to the accompanying drawings, in which example embodiments are shown. Example embodiments may, however, be embodied in many different forms and should not be construed as limited to example embodiments set forth herein. In the drawings, the sizes and relative sizes of layers and regions may be exaggerated for clarity.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, or as "contacting" another element or layer, there are no intervening elements or layers present. Like numerals refer to like elements throughout. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. Unless the context indicates otherwise, these terms are only used to distinguish one element, component, region, layer or section from another region, layer or section, for example as a naming convention. Thus, a first element, component, region, layer or section discussed below in one part of the specification could be termed a second element, component, region, layer or section in another part of the specification or in the claims without departing from the teachings of example embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular example embodiments only and is not intended to be limiting of example embodiments. As used herein, the singular forms "a," "an" and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized example embodiments (and intermediate structures). As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. Thus, the regions illustrated in the figures are schematic in nature and their shapes are not intended to limit the scope of example embodiments.

Terms such as "same," "equal," "planar," or "coplanar," as used herein when referring to orientation, layout, location, shapes, sizes, amounts, or other measures do not necessarily mean an exactly identical orientation, layout, location, shape, size, amount, or other measure, but are intended to encompass nearly identical orientation, layout, location, shapes, sizes, amounts, or other measures within acceptable variations that may occur, for example, due to manufacturing processes. The term "substantially" may be used herein to reflect this meaning.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, example embodiments will be explained in detail with reference to the accompanying drawings.

Figure 2:
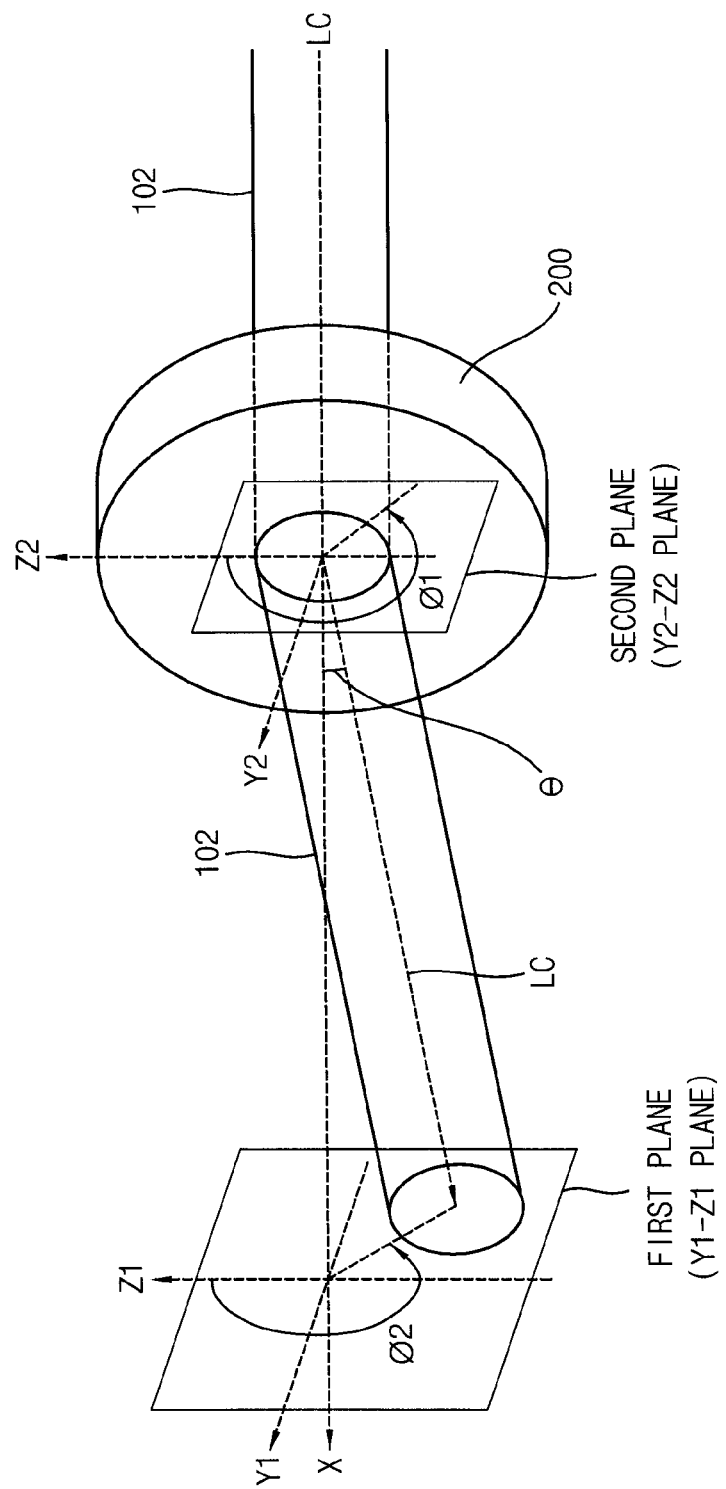
Figure 3:
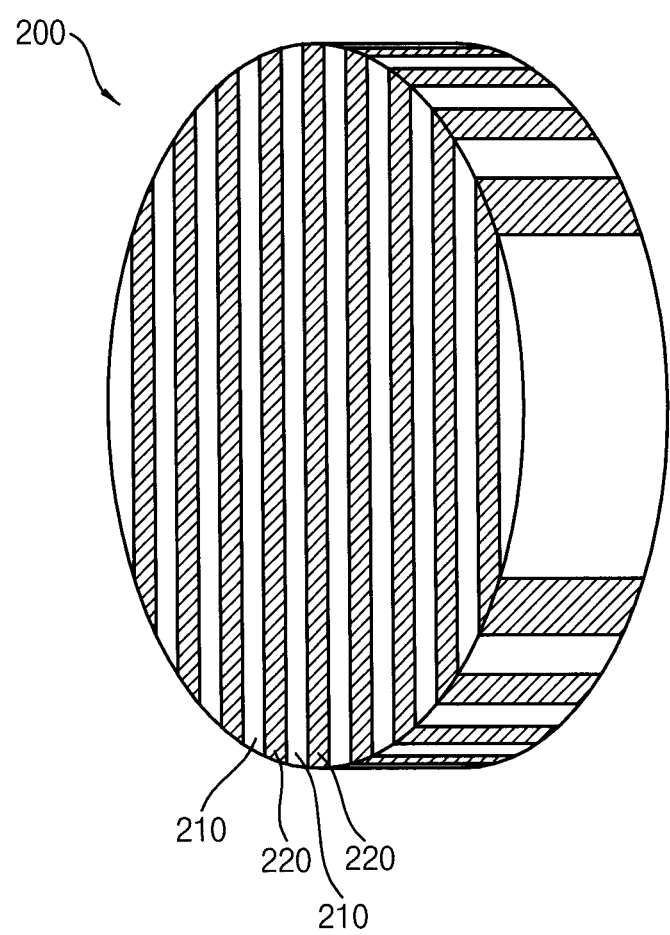
Figure 4:
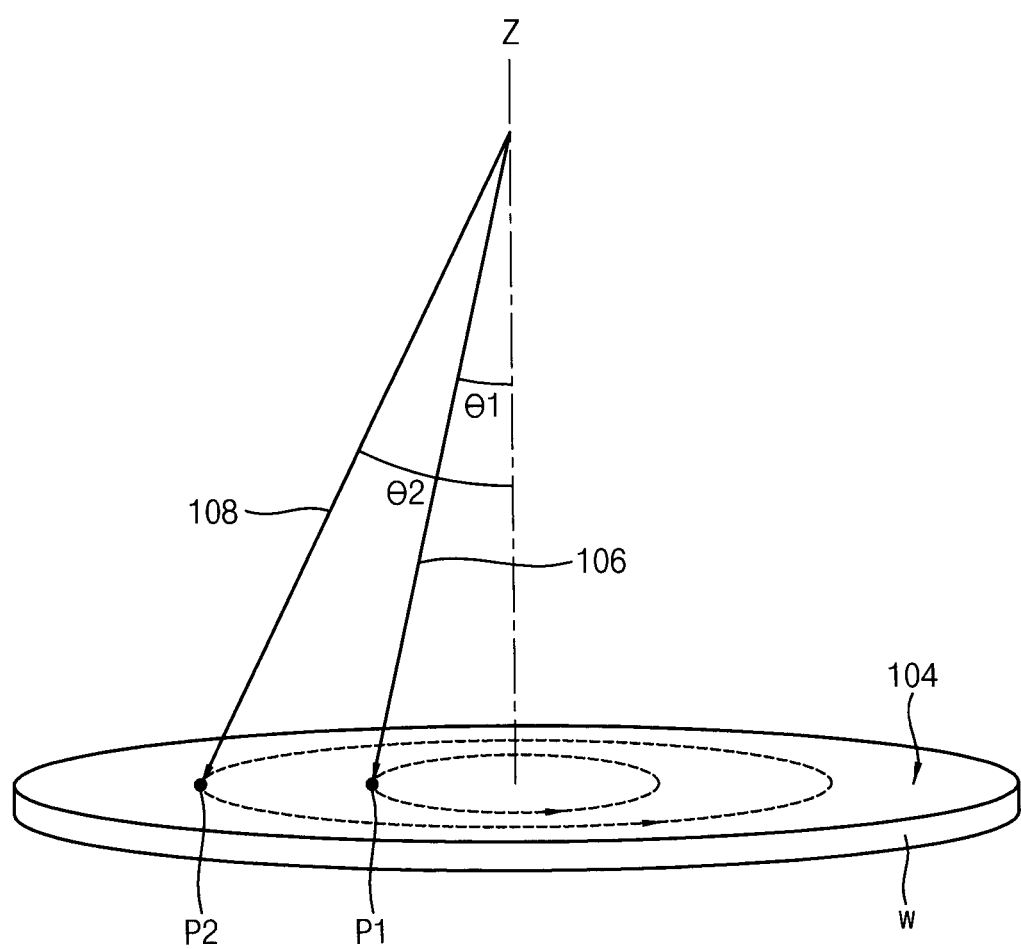
Figure 5:
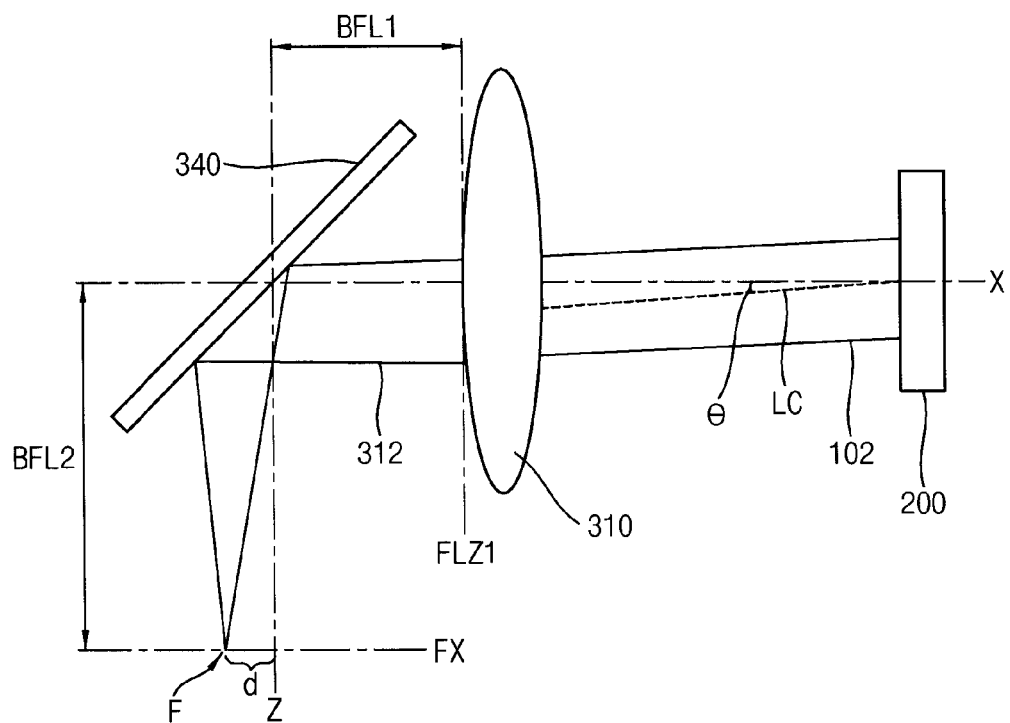
Figure 6:
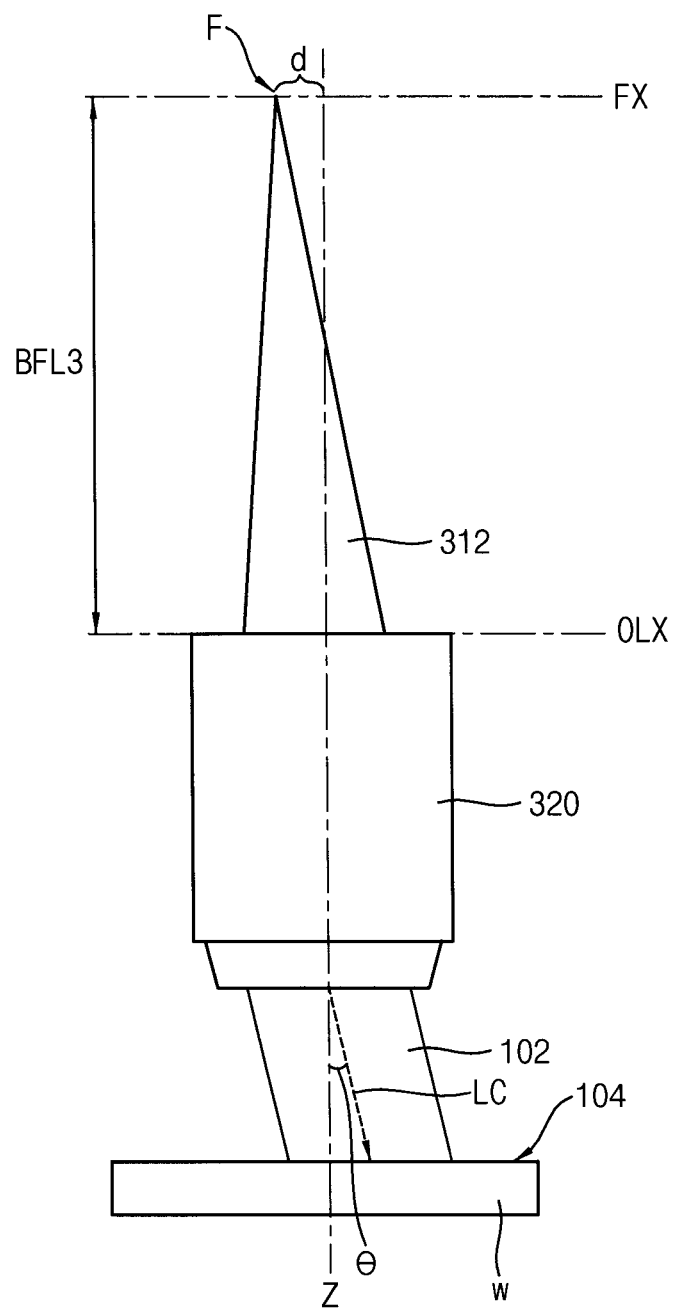

FIG. 1 is a schematic diagram illustrating an optical measurement system in accordance with example embodiments. FIG. 2 is an enlarged perspective view illustrating an 'A' portion in FIG. 1 in accordance with example embodiments. FIG. 3 is a perspective view illustrating a rotating grating of the optical measurement system in FIG. 1 in accordance with example embodiments. FIG. 4 is a view illustrating a parallel light beam incident onto an inspection object in FIG. 1 in accordance with example embodiments. FIG. 5 is an enlarged view illustrating a 'B' portion in FIG. 1 in accordance with example embodiments. FIG. 6 is an enlarged view illustrating a 'C' portion in FIG. 1 in accordance with example embodiments.

Referring to FIGS. 1 to 6, an optical measurement system may include an optical transformation module generating a parallel light beam 102 and transforming the parallel light beam to have a desired incidence angle and a desired incidence position onto a surface 104 of an inspection object W, a lens array 300 focusing the transformed parallel light beam onto the surface 104 of the inspection object W, and a light collector 400 collecting a reflection light 302 from the surface 104 of the inspection object W. The optical transformation module may include a light generator 100 generating the parallel light beam 102, and a rotating grating 200 positioned on a path of the parallel light beam and transforming the parallel light beam to have a desired incidence angle and a desired incidence position onto the surface 104 of the inspection object W.

The light generator 100 may generate the parallel light beam 102 to be incident onto the surface 104 of the inspection object W and may change a wavelength of the parallel light beam 102. The light generator 100 may include a light source 110 generating a light 112 and configured to select between wavelengths of light, in order to change a wavelength of the light 112, and a collimating lens 120 positioned on a path of the light 112 to convert the light 112 into the parallel light beam having the selected wavelength. For example, the light source 110 may produce a visible light source. Alternatively, the light source 110 may produce an ultra violet (UV) or extreme ultra violet (EUV) light source. For example, the light generator 100 may include a laser source which generates a laser beam and changes a wavelength of the laser beam to select a desired wavelength. The light generator 100 may further include a photonic crystal fiber to generate a light having a desired light distribution characteristic.

The rotating grating 200 is positioned on a path of the parallel light beam 102 to change an incidence angle ($\theta$) with respect to the surface 104 of the inspection object W according to the wavelength of the parallel light beam 102.

As illustrated in FIG. 3, the rotating grating 200 may include a plurality of regions which are arranged alternately in a direction. The regions may have different refractive indices respectively. For example, a first region 210 may have a first refractive index and a second region 220 may have a second refractive index different from the first refractive index. The first and second regions 210 and 220 may be arranged alternately with respect to each other. For example, they may extend in one direction (e.g., parallel to each other) and may be arranged in a second direction (e.g., a direction perpendicular to the direction in which they extend).

Alternatively, or additionally, the first region 210 may have a first transmittance and the second region 220 may have a second transmittance different from the first transmittance. Or, the first region 210 may have a first thickness and the second region 220 may have a second thickness different from the first thickness. In certain embodiments, the rotating grating 200 may have a striped pattern. In other embodiments, the rotating grating 200 may have a grid pattern.

For example, the first region 210 and the second region 220 may include a glass material. In certain embodiments, the first region 210 and the second region 220 may have a width of several micrometers.

A lithography process may be performed on, for example, a glass plate using a laser to form a groove, thereby forming the rotating grating 200. For example, the region in which the groove is formed may be the first region 210 and the region in which the groove is not formed may be the second region 220.

According to Snell's law, when the parallel light beam 102 passes through the rotating grating 200, the incidence angle ($\theta$) with respect to the surface 104 of the inspection object W may be changed according to the wavelength of the parallel light beam 102. For example, the greater the wavelength is, the less the incidence angle ($\theta$) with respect to the surface 104 of the inspection object W is. Accordingly, as the wavelength of the parallel light beam 102 is changed in the light generator 100, the incidence angle ($\theta$) of the parallel light beam 102 passing through the rotating grating 200 may be changed according to the wavelength. For example, the parallel light beam 102 may be incident onto the surface 104 of the inspection object W at a one-dimensionally changeable incidence angle due to the change of the wavelength of the parallel light beam 102.

The rotating grating 200 may be positioned on the path of the parallel light beam 102 and may be rotatable by a predetermined rotation angle ($\Phi 1$) to change an incidence position of the parallel light beam 102 with respect to the surface 104 of the inspection object W according to the rotation angle ($\Phi 1$). For example, if the rotating grating 200 is rotated by a rotation angle ($\Phi 1$), the incidence position may be changed by a rotation angle ($\Phi 2$).

As illustrated in FIG. 2, before passing through the rotating grating 200, the parallel light beam 102 may travel along an X-axis. That is, a primary axis LC of the parallel light beam 102 before passing through the rotating grating 200 may be substantially parallel with X-axis. After the parallel light beam 102 passes through the rotating grating 200, the parallel light beam 102 may travel such that the primary axis LC of the parallel light beam 102 makes an incidence angle ($\theta$) with an X-axis perpendicular to a first plane (Y1-Z1 plane).

In one embodiment, the rotating grating 200 may be provided to rotate a predetermined rotation angle ($\Phi 1$). When the rotating grating 200 is rotated by a predetermined rotation angle ($\Phi 1$) from the Z2-axis on a second plane (Y2-Z2 plane), the primary axis LC of the parallel light beam 102 may be rotated by a rotation angle ($\Phi 2$) from the Z1-axis on the first plane (Y1-Z1 plane), and thus, the parallel light beam 102 may be incident onto the surface 104 at the changed point of incidence, which is rotated by the rotation of the primary axis LC from Z1-axis.

Accordingly, the rotating grating 200 may be rotatably provided such that the incidence angle ($\theta$) and the incidence position of the parallel light beam 102 with respect to the surface 104 of the inspection object W may be adjusted according to the wavelength of the parallel light beam 102 and the rotation angle ($\Phi 1$) of the rotating grating 200.

For example, as illustrated in FIG. 4, after a parallel light beam 106 having a first wavelength generated by the light generator 100 passes through the rotating grating 200, the parallel light beam 106 may be incident onto the surface 104 of the inspection object W at an incidence angle ($\theta 1$). If the rotating grating 200 rotates, an incidence position P1 of the parallel light beam 106 with respect to the surface 104 of the inspection object W may be rotated due to the rotation of the rotating grating 200. Accordingly, the parallel light beam 106 may be incident onto the surface 104 of the inspection object W at the incidence angle ($\theta 1$) and the incidence position (P1), or at other positions along the dotted line to which P1 is part of. For example, the dotted line may have a circular or oval shape.

After a parallel light beam 108 having a second wavelength greater than the first wavelength generated by the light generator 100 passes through the rotating grating 200, the parallel light beam 108 may be incident onto the surface 104 of the inspection object W at an incidence angle ($\theta 2$). If the rotating grating 200 rotates, an incidence position P2 of the parallel light beam 108 with respect to the surface 104 of the inspection object W may be rotated due to the rotation of the rotating grating 200. Accordingly, the parallel light beam 108 may be incident onto the surface 104 of the inspection object W at the incidence angle (θ2) and the incidence position (P2), or at other positions along the dotted line to which P2 is part of. For example, the dotted line may have a circular or oval shape.

Thus, a parallel light beam having various incidence angles with respect to the surface 104 of the inspection object W may be incident onto the whole surface 104 of the inspection object W.

As illustrated in FIG. 1, the lens array 300 may have various lenses for directing the parallel light beam 102 to the incidence position at the incidence angle (θ) and focusing the parallel light beam 102 to form a clear image. For example, the lens array 300 may include a focusing lens 310, an objective lens 320 and an ocular lens 330. The inspection object W may include a wafer having a fine pattern formed thereon. For example, the inspection object W may be a semiconductor device such as an integrated circuit on a semiconductor chip on a die that is part of a wafer, or that is already separated from a wafer.

As used herein, a semiconductor device may refer to a device such as a semiconductor chip (e.g., memory chip and/or logic chip formed on a die), a stack of semiconductor chips, a semiconductor package including one or more semiconductor chips stacked on a package substrate, or a package-on-package device including a plurality of packages. These devices may be formed using ball grid arrays, wire bonding, through substrate vias, or other electrical connection elements, and may include memory devices such as volatile or non-volatile memory devices.

An electronic device, as used herein, may refer to these semiconductor devices, but may additionally include products that include these devices, such as a memory module, memory card, hard drive including additional components, or a mobile phone, laptop, tablet, desktop, camera, or other consumer electronic device, etc.

In example embodiments, the lens array 300 may include the focusing lens 310 positioned on a path of the parallel light beam 102 passing through the rotating grating 200 to convert the parallel light beam 102 into a convergent/divergent light beam 312, the objective lens 320 positioned on a path of the convergent/divergent light beam 312 to convert again the convergent/divergent light beam 312 into the parallel light beam 102 and convert a light beam 302 reflecting from the surface 104 of the inspection object W into a reflecting parallel light beam 322, and the ocular lens 330 positioned on a path of the reflecting parallel light beam 322 to convert the reflecting parallel light beam 322 into a reflecting non-parallel light beam 302.

The lens array 300 may further include a beam splitter 340 which is positioned between the focusing lens 310 and the objective lens 320 to reflect the convergent/divergent light beam 312 to the objective lens 320.

The focusing lens 310 may be positioned on the path of the parallel light beam 102 passing through the rotating grating 200 to convert the parallel light beam 102 into a convergent/divergent light beam 312 and control a focal position of the convergent/divergent light beam 312.

As illustrated in FIG. 5, as the parallel light beam 102 travels such that the primary axis LC of the parallel light beam 102 makes an incidence angle (θ) with the X-axis and passes through the focusing lens 310, the parallel light beam 102 may be converted into the convergent/divergent light beam 312. The incidence angle (θ) of the parallel light beam 102, a distance d of the focal point of the convergent/divergent light beam 312 and the back focal length (BFL, which equals BFL1+BFL2) of the focusing lens 310 may be expressed by following Equation 1.

$$\tan\theta = \frac{d}{BFL} = \frac{d}{BFL1 + BFL2} \quad \text{[Equation 1]}$$

where, θ is the incidence angle of the parallel light beam from X-axis, d is a distance of the focus (F) from Z-axis, BFL is the back focal length of the focusing lens (BFL1+BFL2), BFL1 is a distance from FLZ1-axis to Z-axis, and BFL2 is a distance from X-axis to FX-axis.

The change of the incidence angle (θ) of the parallel light beam 102 from the X-axis may be represented as the change of the distance d of the focal point of the convergent/divergent light beam 312. Accordingly, the focusing lens 310 may be moved along X-axis such that the distance d of the focal point may be adjusted to obtain a clear image from the surface of the inspection object W.

The objective lens 320 may be positioned on the path of the convergent/divergent light beam 312 to convert again the convergent/divergent light beam 312 into the parallel light beam 102, direct the parallel light beam 102 to the inspection object W at the incidence angle (θ) and convert the light beam 302 reflecting from the surface 104 of the inspection object W into the reflecting parallel light beam 322.

As illustrated in FIG. 5, as the convergent/divergent light beam 312 having the distance of the focal point passes through the objective lens 320, the convergent/divergent light beam 312 may be converted again into the parallel light beam 102 having the incidence angle (θ) with respect to the surface 10 of the inspection object W, for example, the incidence angle (θ) from Z-axis. The incidence angle (θ) of the parallel light beam 102, the distance d of the focal point of the convergent/divergent light beam 312 and the back focal length (BFL) of the focusing lens 310 may be expressed in following Equation 2.

$$\tan\theta = \frac{d}{BFL3} \quad \text{[Equation 2]}$$

where, θ is the incidence angle of the parallel light beam onto the inspection object, d is a distance of the focal point of the convergent/divergent light beam (distance of the focus (F) from Z-axis), and BFL is the back focal length of the objective lens (distance from FX-axis to OLX-axis).

Accordingly, the objective lens 320 may be moved along Z-axis such that the distance d of the focal point may be adjusted to obtain a clear image from the surface 104 of the inspection object W.

As illustrated in FIG. 1, the objective lens 320 may convert the light beam 302 reflecting from the inspection object W into the reflecting parallel light beam 322 and direct the reflecting parallel light beam 322 to the collector 400.

The ocular lens 330 may be positioned on the path of the reflecting parallel light beam 322 to convert again the reflecting parallel light beam 322 into the reflecting light beam (e.g., non-parallel light beam) 302. The ocular lens 330 may be moved along Z-axis to control the focal point to thereby obtain a clear image from the surface 104 of the inspection object W.

The collector 400 may collect the reflecting light beam 302 converted from the reflecting parallel light beam 322 passing through the ocular lens 330. For example, the reflecting light beam 302 may have image information of the surface 104 of the inspection object W. The collector 400 may detect defects on the surface 104 of the inspection object W based on the image information.

In example embodiments, the optical measurement system may include the light generator 110 generating the parallel light beam 102 and changing the wavelength of the parallel light beam 102 and the rotating grating 200 rotatably provided on the path of the parallel light beam. If the wavelength of the parallel light beam is changed, the parallel light beam 102 passing through the rotating grating 200 may be refracted according to the wavelength to change the incidence angle of the parallel light beam 102 with respect to the surface 104 of the inspection object W. If the rotating grating 200 rotates, an incidence position the parallel light beam 102 with respect to the surface 104 of the inspection object W may be rotated due to the rotation of the rotating grating 200.

The incidence angle ($\theta$) of the parallel light beam 102 with respect to the surface 104 of the inspection object W may be changed using the difference of the refractive index, to thereby reduce optical losses of the parallel light beam 102. The rotating grating 200 may be rotatable to change an incidence position of the parallel light beam 102 with respect to the surface 104 of the inspection object W, thereby scanning the surface 104 of the inspection object W at a high speed.

Hereinafter, a method of inspecting a surface of an inspection object using the optical measurement system in FIG. 1 will be explained. Furthermore, a method of manufacturing a semiconductor device by inspecting a surface of an inspection object using the optical measurement system in FIG. 1 will be explained.

Figure 7:
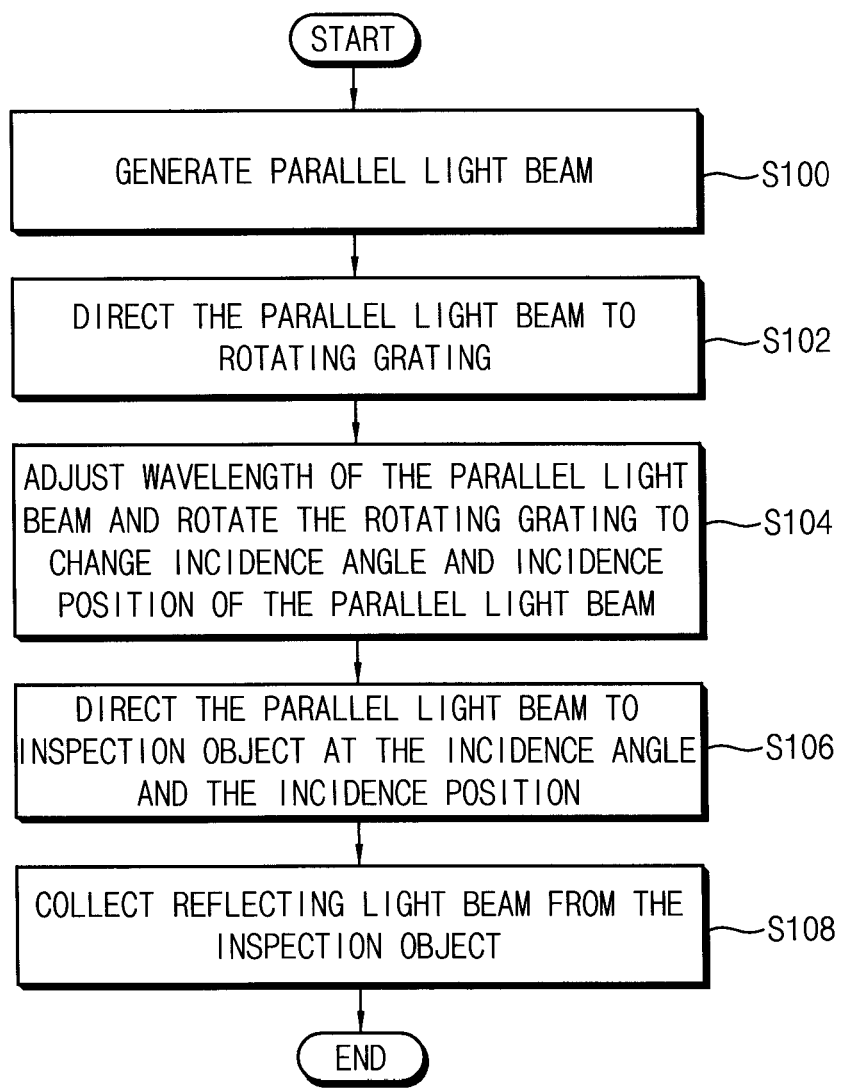

FIG. 7 is a flowchart illustrating an optical measurement method in accordance with example embodiments.

Referring to FIGS. 1, 2 and 7, a light generator 100 may generate a parallel light beam 102 (S100). The light generator 100 may be configured to change a wavelength of the parallel light beam 102.

For example, a light 112 generated by a light source 110 may pass through a collimating lens 120 to be converted into the parallel light beam 102. Alternatively, the parallel light beam 102 may be generated by a laser source (not illustrated).

Then, the parallel light beam 102 is incident onto a rotating grating 200 which may be provided to be rotatable by a predetermined rotation angle (S102). The rotating grating 200 may be, for example, a light-beam aiming device configured to re-aim a light beam entering the light-beam aiming device at a first linear direction, so that the light beam exits the light-beam aiming device at a different linear direction. In certain embodiments, as described above, the aiming may be accomplished based on a wavelength of light used and a positioning of the light-beam aiming device (e.g., a rotation). In certain embodiments, the light-beam aiming device may have a plate shape, and/or may be rotatable, such as shown and described with respect to FIGS. 2 and 3. However, other shapes and/or configurations for moving the light-beam aiming device may be used.

In certain embodiments, the wavelength of the parallel light beam 102 and the rotation angle of the rotating grating 200 may be controlled to adjust an incidence angle and an incidence position of the parallel light beam on a surface 104 of an inspection object W (S104). As such, the wavelength of light and a positioning or configuration of an optical component such as a light-beam aiming device may be used to aim, or adjust the vector direction of, the light incident the aiming device.

The rotating grating 200 may be positioned on a path of the parallel light beam 102 and may be rotatable by a predetermined rotation angle ($\Phi A$) to change the incidence angle ($\theta$) and the incidence position of the parallel light beam 102 with respect to the surface 104 of the inspection object W according to the wavelength of the parallel light beam 102 and the rotation angle ($\Phi 1$).

According to Snell's law, when the parallel light beam 102 passes through the rotating grating 200, the incidence angle ($\theta$) with respect to the surface 104 of the inspection object W may be changed according to the wavelength of the parallel light beam 102. For example, the greater the wavelength is, the less the incidence angle ($\theta$) with respect to the surface 104 of the inspection object W is. Accordingly, as the wavelength of the parallel light beam 102 is changed in the light generator 100, the incidence angle ($\theta$) of the parallel light beam 102 passing through the rotating grating 200 may be changed according to the wavelength. As such, the parallel light beam 102 may be incident onto the surface 104 of the inspection object W at a one-dimensionally changeable incidence angle due to the change of the wavelength of the parallel light beam 102.

The rotating grating 200 may be positioned on the path of the parallel light beam 102 and may be rotated a predetermined rotation angle ($\Phi 1$) to change an incidence position of the parallel light beam 102 with respect to the surface 104 of the inspection object W according to the rotation angle ($\Phi 1$). For example, if the rotating grating 200 is rotated by a rotation angle ($\Phi 1$), the incidence position may be changed by the rotation angle ($\Phi 1$).

As illustrated in FIG. 2, the parallel light beam 102 may travel along X-axis before passing through the rotating grating 200. That is, a primary axis LC of the parallel light beam 102 before passing through the rotating grating 200 may be substantially parallel with X-axis. After the parallel light beam 102 passes through the rotating grating 200, the parallel light beam 102 may travel such that the primary axis LC of the parallel light beam 102 may make an incidence angle ($\theta$) with X-axis perpendicular to a first plane (Y1-Z1 plane).

The rotating grating 200 may be provided to rotate a predetermined rotation angle ($\Phi 1$). When the rotating grating 200 is rotated by a predetermined rotation angle ($\Phi 1$) from Z2-axis on a second plane (Y2-Z2 plane), the primary axis LC of the parallel light beam 102 may be rotated by a rotation angle ($\Phi 2$) from Z1-axis on the first plane (Y1-Z1 plane), and thus, the parallel light beam 102 may be incident onto the surface 104 at the changed point of incidence, which is rotated according to the rotation of the primary axis LC from Z1-axis.

Accordingly, the rotating grating 200 may be rotatably provided such that the incidence angle ($\theta$) and the incidence position of the parallel light beam 102 with respect to the surface 104 of the inspection object W may be adjusted according to the wavelength of the parallel light beam 102 and the rotation angle ($\Phi 1$) of the rotating grating 200.

Then, the parallel light beam 102 may be incident onto the surface 104 of the inspection object W at the incidence angle ($\theta$) and the incident position (S106), resulting in two-dimensional control of the parallel light beam 102.

In example embodiments, the parallel light beam 102 may be incident onto the surface 104 of the inspection object W through a lens array 300. For example, the lens array 300 may include a focusing lens 310, an objective lens 320, and an ocular lens 330. In particular, the parallel light beam 102 may be converted into a convergent/divergent light beam 312 using the focusing lens 310. Then, the convergent/divergent light beam 312 may be converted again into the parallel light beam 102 using the objective lens 320, and then, a light beam 302 reflecting from the surface 104 of the inspection object W may be converted into a reflecting parallel light beam 322 using the objective lens 320. Then, the reflecting parallel light beam 322 may be converted into a reflecting light beam 302 using the ocular lens 330.

The positions of the focusing lens 310, the objective lens 320, and the ocular lens 330 may be controlled to obtain a clear image from the surface 104 of the inspection object W.

Then, the reflecting light beam 302 converted from the reflecting parallel light beam 322 passing through the ocular lens 330 may be collected using a collector 400. For example, the reflecting light beam 302 may have image information of the surface 104 of the inspection object W. The collector 400 may detect defects on the surface 104 of the inspection object W based on the image information.

In example embodiments, the parallel light beam 102 may be generated and the wavelength of the parallel light beam 102 may be changed. The parallel light beam 102 may pass through the rotating grating 200 rotatably provided on the path of the parallel light beam 102. If the wavelength of the parallel light beam is changed, the parallel light beam 102 passing through the rotating grating 200 may be refracted according to the wavelength to change the incidence angle of the parallel light beam 102 with respect to the surface 104 of the inspection object W. If the rotating grating 200 rotates, an incidence position the parallel light beam 102 with respect to the surface 104 of the inspection object W may be rotated due to the rotation of the rotating grating 200.

The incidence angle ($\theta$) of the parallel light beam 102 with respect to the surface 104 of the inspection object W may be changed using the difference of the refractive index, to thereby reduce optical losses of the parallel light beam 102. The rotating grating 200 may be rotated to change an incidence position of the parallel light beam 102 with respect to the surface 104 of the inspection object W, thereby two-dimensionally scanning the whole surface 104 of the inspection object W at a high speed.

Figure 8:
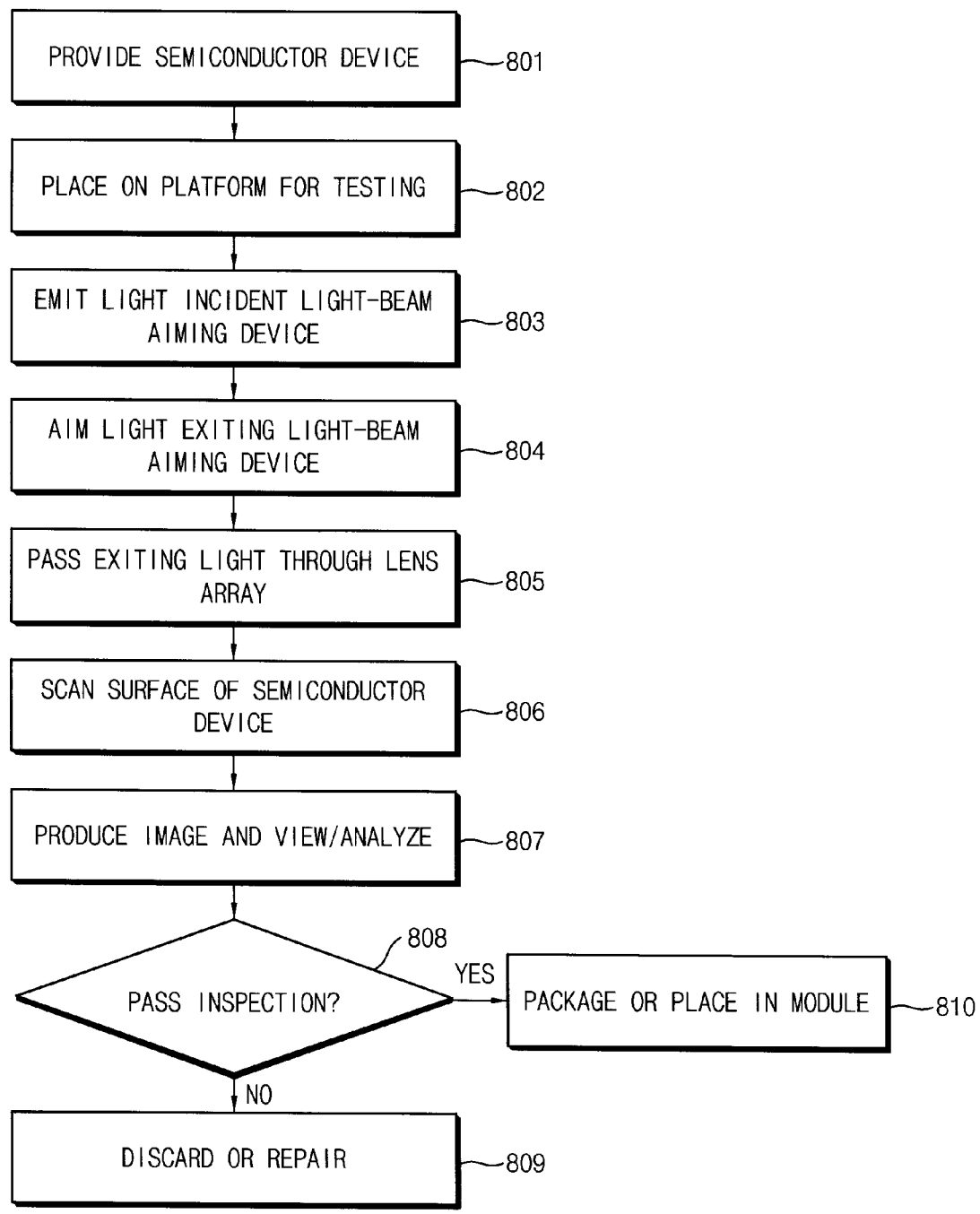

FIG. 8 depicts a method of manufacturing a semiconductor device, according to certain disclosed embodiments.

As depicted in FIG. 8, in step 801, a semiconductor device, such as a semiconductor chip, is provided. The semiconductor chip may be, for example, a memory chip or a logic chip. The semiconductor chip may be formed of a die from a wafer, and may include an integrated circuit thereon. For example, the semiconductor chip may be part of a wafer, or may be in singulated form. In step 802, the semiconductor chip may be placed on a test platform for testing, or may be otherwise mobilized for testing. In step 803, a light for scanning the semiconductor chip is emitted from a light source (e.g., 110) of a light generator, and is incident a light-beam aiming device. The light generator may be configured to select among different wavelengths for the light. The light-beam aiming device may have a plate shape, and may be a rotating grating, such as item 200 shown in FIG. 3, for example. The light received by the light-beam aiming device may be a parallel light beam having a particular selected wavelength. In step 804, based on the selected wavelength of the light and the positioning of the light-beam aiming device, the light exiting the light-beam aiming device is aimed to have a vector direction different from the incident direction of the light-beam. In step 805, the exiting light beam passes through a lens array (e.g., 300), and a surface of the semiconductor chip is scanned using the light.

In certain embodiments, an entire surface, or at least desired portions of the surface, can be scanned (step 806) in a two-dimensional manner using the light-beam aiming device to control the positioning of the light beam throughout the surface of the semiconductor chip. In step 807, based on the scanning, an image may be produced of the surface of the semiconductor chip, and the image may be collected by a light collector (e.g., 400), and may be viewed and/or analyzed. It can then be determined (step 808) if the semiconductor chip passes inspection (e.g., by analyzing for defects on the surface). If it fails inspection (step 809), the semiconductor chip may be discarded or fixed. If the semiconductor chip passes inspection (step 810), it may then be packaged, for example, by being singulated if it was not already singulated, being placed on a substrate, and being covered with a protective mold. For example, the semiconductor chip may be included in a single or multi-chip package, or package-on-package device such that it is mounted on a semiconductor substrate, and covered by a protective mold. Or, the semiconductor chip may be placed in a module on a substrate such as a module board. As such, the semiconductor chip may be included in an electronic device, such as a semiconductor package or a semiconductor module (e.g., a memory module).

While example embodiments have been particularly shown and described, it will be understood by one of ordinary skill in the art that variations in form and detail may be made therein without departing from the spirit and scope of the claims.

What is claimed is:

1. An optical measurement system, comprising:
   an optical transformation module configured to generate a parallel light beam to be incident onto a surface of an inspection object and adjust an incidence angle and an incidence position of the parallel light beam with respect to the surface; and
   a collector configured to collect a reflecting light beam from the surface of the inspection object,
   wherein the optical transformation module comprises:
      a light generator configured to generate the parallel light beam and change a wavelength of the parallel light beam;
      a rotating grating positioned on a path of the parallel light beam and configured to rotate by a rotation angle such that the parallel light beam is transformed, based on the wavelength of the parallel light beam and the rotation angle of the rotating grating, to have a desired incidence angle and a desired incidence position onto the surface of the inspection object; and
      a lens array through which the parallel light beam is incident onto the surface of the inspection object at the incidence angle and the incidence position,
   wherein the rotating grating has a central axis perpendicular to the light generator,
   wherein the rotating grating is further configured to rotate by the rotation angle around the central axis, and
   wherein the lens array comprises:
      a focusing lens positioned on a path of the parallel light beam passing through the rotating grating and configured to convert the parallel light beam into a converted convergent/divergent light beam;
      an objective lens positioned on a path of the converted convergent/divergent light beam and configured to convert again the converted convergent/divergent light beam into the parallel light beam, direct the parallel light beam to the inspection object at the incidence angle and the incidence position, and convert a light beam reflecting from the inspection object into a reflecting parallel light beam; and an ocular lens positioned on a path of the reflecting parallel light beam and configured to convert the reflecting parallel light beam into a reflecting light beam.

2. The optical measurement system of claim 1, wherein the rotating grating comprises a plurality of regions which are arranged alternately in a direction and have different refractive indices respectively.

3. The optical measurement system of claim 1, wherein the rotating grating comprises a plurality of regions which are arranged alternately in a direction and have different transmittances respectively.

4. The optical measurement system of claim 1, wherein the rotating grating has a striped or grid pattern.

5. The optical measurement system of claim 1, wherein the light generator comprises:

a light source configured to generate a light and change a wavelength of the light; and a collimating lens positioned on a path of the light and configured to convert the light into the parallel light beam having the wavelength.

6. The optical measurement system of claim 1, wherein the light generator comprises a laser source configured to generate a laser beam and changes a wavelength of the laser beam.

7. The optical measurement system of claim 1, further comprising:

a beam splitter which is positioned between the focusing lens and the objective lens and configured to reflect the convergent/divergent light beam passing through the focusing lens to the objective lens as the converted convergent/divergent light beam.

8. The optical measurement system of claim 7, wherein the reflecting light beam has image information of the inspection object, and the collector comprises a charge coupled device (CCD) lens configured to collect the image information of the inspection object from the reflecting light beam.

* * * * *